United States Patent [19]
Foxall et al.

[11] Patent Number: 5,985,569
[45] Date of Patent: Nov. 16, 1999

[54] PRIMERS FOR AMPLIFICATION OF A GENUS SPECIFIC SEQUENCE OF THE MYCOBACTERIUM 16S RRNA GENE

[75] Inventors: Paul A. Foxall, San Mateo, Calif.; Harish Kumar, Tarrytown, N.Y.

[73] Assignee: Becton, Dickinson and Company, Franklin Lakes, N.J.

[21] Appl. No.: 08/938,858

[22] Filed: Sep. 26, 1997

[51] Int. Cl.$^6$ .............................. C12Q 1/68; C07H 21/02; C07H 21/04; C12P 19/34
[52] U.S. Cl. ............................ 435/6; 536/23.1; 536/24.3; 435/91.2
[58] Field of Search .................................. 536/22.1, 24.3, 536/24.32, 25.32; 435/91.2, 6

[56] References Cited

U.S. PATENT DOCUMENTS

| | | | |
|---|---|---|---|
| 5,521,300 | 5/1996 | Shah et al. ............................ | 536/24.32 |
| 5,667,994 | 9/1997 | Dilly et al. .............................. | 435/91.2 |

FOREIGN PATENT DOCUMENTS

| | | |
|---|---|---|
| 0 528 306 A2 | 2/1993 | European Pat. Off. . |
| 0 529 985 A1 | 3/1993 | European Pat. Off. . |
| WO 93/04201 | 3/1993 | WIPO . |
| WO 95/31571 | 11/1995 | WIPO . |

OTHER PUBLICATIONS

B. Springer, et al. "Two–Laboratory Collaborative Study on Identification of Mycobacteria: Molecular versus Phenotypic Methods" *J. Clin. Microbiol.* 34:296–303 (1996).

W. R. Butler, et al. "Cross–Reactivity of Genetic Probe for Detection of *Mycobacterium tuberculosis* with Newly Described Species of *Mycobacterium celatum*" *J. Clin. Microbiol.* 32:536–538 (1994).

C. Martin, et al. "False Positive Result of *Mycobacterium tuberculosis* Complex DNA Probe Hybridization with a *Mycobacterium terrae* Isolate" *Eur. J. Clin. Microbiol. Infect. Dis.* 12:309–310 (1993).

S. D. Lim, et al. "Genotypic Identification of Pathogenic Mycobacterium Species by Using a Nonradioactive Oligonucleotide Probe" *J. Clin. Microbiol.* 29:1276–1278 (1991).

C. E. Musial, et al. "Identification of Mycobacteria from Culture by Using the Gen–Probe Rapid Diagnostic System for *Mycobacterium avium* Complex and *Mycobacterium tuberculosis* Complex" *J. Clin. Microbiol.* 26:2120–2123 (1988).

V. Jonas, et al. "Detection and Identification of *Mycobacterium tuberculosis* Directly from Sputum Sediments by Amplification of rRNA" *J. Clin. Microbiol.* 31:2410–2416 (1993).

P. Kirschner, et al. "Diagnosis of Mycobacterial Infections by Nucleic Acid Amplification: 18 Month Prospective Study" *J. Clin. Microbiol.* 34:304–312 (1996).

E. Avaniss–Aghajani, et al. "Molecular Technique for Rapid Identification of Mycobacteria" *J. Clin. Microbiol.* 34:98–102 (1996).

B. Boddinghaus, et al. "Detection and Identification of Mycobacteria by Amplification of rRNA" *J. Clin. Microbiol.* 28:1751–1759 (1990).

*Primary Examiner*—W. Gary Jones
*Assistant Examiner*—Ethan Whisenant
*Attorney, Agent, or Firm*—Donna R. Fugit

[57] ABSTRACT

Disclosed herein are oligonucleotide primers and probes that can be used to detect species of medical interest in the genus Mycobacterium. Also disclosed are genus-specific methods and kits for detecting Mycobacterium using the disclosed oligonucleotide primers and probes. Preferably, Mycobacterium are detected by amplifying the Mycobactenium nucleic acids using the disclosed amplification primers, and then detecting the amplified nucleic acids. In a more preferred embodiment, Mycobacterium nucleic acids are amplified and detected by thermophilic strand displacement amplification.

25 Claims, 3 Drawing Sheets

FIG-3

```
          10         20         30         40         50         60         70         80         90        100
1234567890 1234567890 1234567890 1234567890 1234567890 1234567890 1234567890 1234567890 1234567890 1234567890
GGCGGCCGTGCTTAACACATG CAAGTCGAACGAAAGGTCT CTTCGGAGATACTCGAGTGG CGAACGGGTGAGTAACACGT GGGTGATCTGCCCTGCACTT   100
CGGGATAAGCCTGGGAAACT GGGTCTAATACCGGATAGA CCACGGGATGCATGTCTTGT GGTGGAAAGCGCTTTAGCGG TGTGGGATGAGCCCGGCGCC   200
TATCAGCTTGTTGGTGGGGT GACGGGCTACCAAGGCGACG ACGGGTAGCCGGCCTGAGAG GGTGTCCGGCCACACTGGGA CTGAGATACGGCCCAGACTC   300
CTACGGGAGGCAGCAGTGGG GAATATTGCACAATGGGCGC AAGCCTGATGCAGCGACGCC GCGTGGGGGATGACGGCCTT CGGGTTGTAAACCTCTTTCA   400
CCATCGACGAAGTCCGGGT TCTCTCGGATTGACGGTAGG TGGAGAAGAAGCACCGGCCA ACTACGTGCCAGCAGCCGCG GTAATACGTAGGGTGCGAGC   500
GTTGTCCGGAATTACTGGGC GTAAAGAGCTCGTAGGTGGT TTGTGCGTTGTTCGTGAAA TCTCACGCTTAACTGTGAG CGTGCGGGCGATACGGCAG   600
ACTAGAGTACTGCAGGGGAG ACTGGAATTCCTGGTGTAGC GGTGGAATGCGCAGATATCA GGAGGAACACCGGTGGCGAA GGCGGGTCTCTGGGCAGTAA   700
CTGACGCTGAGGAGCGAAAG CGTGGGGAGCGAACAGGATT AGATACCCTGGTAGTCCACG CCGTAAACGGTGGGTACTAG GTGTGGGTTTCCTTCCTTGG   800
GATCCGTGCCGTAGCTAACG CATTAAGTACCCCGCCTGGG GAGTACGGCCGCAAGGCTAA AACTCAAAGGAATTGACGGG GGCCCGCACAAGCGGCGGAG   900
CATGTGGATTAATTCGATGC AACGCGAAGAACCTTACCTG Mg733 AL3 GGTTTGACATGCACAGGACG CGTCTAGAGATAGGCGTTCC CTTGTGTGGCTGTGTGCAGT  1000
AR3  Mg733 BR2      Mg733 BL
GGTGCATGGCTGTCGTCAGC TCGTGTCGTGAGATGTTGGG TTAAGTCCCGCAACGAGCGC AACCCTTGTCTCTCATGTTGCC AGCACGTAATGGTGGGACT  1100
CGTGAGAGACTGCCGGGGTC AACTCGGAGGAAGGTGGGGA TGACGTCAAGTCATCATGCC CCTTATGTCCAGGGCTTCAC ACATGCTACAATGGCCGGTA  1200
CAAAGGGCTGCGATGCCGCG AGGTTAAGCGAATCCTTAAA AGCCGGTCTCAGTTCGGATC GGGGTCTGCAACTCGACCCC GTGAAGTCGGAGTCGCTAGT  1300
AATCGCAGATCAGCAACGCT GCGGTGAATACGTTCCCGGG CCTTGTACACACCGCCCGTC ACGTCATGAAAGTCGGTAAC ACCCGAAGCCAGTGGCCTAA  1400
CCCTCGGGAGGGAGCTGTCG AAGGTGGGATCGGCGATTGG GACGAAGTCGTAACAAGGTA GCCG
```

PRIMERS FOR AMPLIFICATION OF A GENUS SPECIFIC SEQUENCE OF THE MYCOBACTERIUM 16S RRNA GENE

FIELD OF THE INVENTION

The present invention relates to methods and nucleic acid sequences for detecting and/or identifying microorganisms, in particular methods and nucleic acid sequences for detecting and/or identifying microorganisms of the genus Mycobacterium by nucleic acid amplification and nucleic acid hybridization.

BACKGROUND OF THE INVENTION

The Mycobacterium are a genus of bacteria that are characterized as acid-fast, non-motile, motile, gram-positive bacillus. The genus comprises many species including *Mycobacterium afiicanum, M. avium, M. bovis, M. bovis-BCG, M. chelonae, M. fortuitum, M. gordonae, M. itracellulare, M. kansasii, M. leprae, M. microti, M. scrofulaceum, M. paratuberculosis,* and *M. tuberculosis*. Some of the mycobacteria are pathogenic in both humans and animals, in particular *M. tuberculosis, M. leprae,* and *M. bovis*. Other mycobacterial species are not normally pathogenic, but cause opportunistic infections in immuno-compromised individuals, such as AIDs patients. For example, infection by *M. kansasii, M. avium,* and *M. intracellulare* can cause severe lung disease in subjects in whom the immune system is suppressed or compromised. In fact, for the first time since 1953, reported cases of mycobacterial infections are increasing in the United States; many of these cases are related to the AIDS epidemic.

Conventional laboratory diagnosis of mycobacteria is based on acid-fast staining and cultivation of the organism, followed by biochemical assays. As a result of the slow growth and long generation time of mycobacteria, accurate laboratory diagnosis of mycobacteria by conventional techniques can take as long as six weeks. Automated culturing systems such as the BACTEC system (Becton Dickinson Microbiology Systems, Sparks, MD) can decrease the time for identification of mycobacteria to one to two weeks. Nevertheless, there still exists a need in the art to reduce the time required for accurate diagnosis of mycobacteria to less than a week, preferably to about one day.

Nucleic acid based diagnostic assays, such as Southern hybridization, offer rapid results, usually in less than one day. Polymerase chain reaction (PCR)-based methods for identifying mycobacteria are even more sensitive and can often provide results within hours. However, nucleic acid based methodologies for diagnosing mycobacteria are often fraught with drawbacks. Most of these methods are costly, are available for only a few species of *Mycobacterium*, and can resolve only one species per sample tested. Moreover, nucleic acid based assays require the development of oligonucleotide probes or primers that are specific for the genus Mycobacterium or for a particular species of Mycobacterium.

Isothermal amplification methods such as strand displacement amplification (SDA) and Self-Sustained Sequence Replication (3SR) have particular advantages in diagnostics, as they do not require the high/low temperature cycling characteristic of methods such as PCR. They are therefore simpler protocols and require less specialized equipment to perform. However, isothermal amplification methods such as SDA generally are not capable of amplifying targets as large as those amplifiable by PCR. Small target sequences severely restrict the ability to design primers and probes with the desired specificity for detection of a given target because the proximity of appropriate amplification primer binding sites becomes a factor, and there is less sequence available in the amplification product for assay probe design.

Initially, SDA was developed for use at temperatures between about 35° C. and 45° C. ("conventional SDA"). Recently, SDA has been adapted to higher temperatures using thermophilic polymerases and restriction endonucleases ("thermophilic SDA" or "tSDA") as described in EP 0 684 315 to Frasier et al. The tSDA system provides the advantages of increased speed and specificity as compared with conventional SDA. While the target binding sequences of amplification primers designed for use in conventional SDA generally will function in tSDA, they are usually shorter and amplification efficiency may therefore be reduced at the higher temperatures of tSDA. In contrast, primers comprising the target binding sequences of primers designed for tSDA usually function efficiently when adapted to amplification primers for conventional SDA or other amplification reactions.

To obviate the problems attendant to conventional diagnosis of Mycobacteinum, there have been attempts to develop nucleic acid based diagnostic methods using genus-specific hybridization or nucleic acid amplification with Mycobacteinum-specific oligonucleotides.

B. Böddinghaus et al. (*J. Clin. Microbiol.* 28, 1751 (1990)) disclose Mycobacterium genus-specific oligonucleotides derived from 16S rRNA sequences that specifically amplify and hybridize to mycobacterial DNA.

WO 95/31571 teaches oligonucleotides and methods for detecting species of Mycobacterium by ligase chain reaction. Oligonucleotides were selected from the DNA sequences of the *M. tuberculosis* protein antigen b gene, *M. bovis* IS987 direct repeat sequence, *M. tuberculosis* IS-like IS6110 element, *M. tuberculosis* 16S rRNA gene, M. tuberculosis 65 kDa heat shock gene, and the *M. tuberculosis* 10 kDa heat shock protein gene.

M. Hughes et al. (*J. Clin. Microbiol.* 31, 3216 (1993)) disclose methods of typing species within the genus Mycobacterium. Polymerase chain reaction with genus-specific primers is performed to amplify the 16S rRNA gene, followed by either restriction enzyme analysis or direct cycle sequencing to identify various mycobacterial species. These methods required 48 and 72 hours, respectively, to complete.

T. Rogall et al. (*J. Gen. Microbiol.* 136, 1915 (1990)) and P. Kirschner et al. (*J. Clin. Microbiol.* 31, 2882 (1993)) concern methods of identifying species of Mycobacterium using direct sequencing of PCR-amplified fragments of the 16S rRNA gene. Likewise, M. Vaneechoutte et al., (*J. Clin. Microbiol.* 31, 2061 (1993)) and E. Avaniss-Aghajani et al. (*J. Clin. Microbiol.* 34, 98–102 (1996)) teach methods of identifymg specific mycobacterial species by PCR amplification of a region of the 16S rRNA gene combined with restriction analysis of the amplification products.

U.S. Pat. No. 5,422,242 to Young teaches a two-step method for identifying species of Mycobacterium. First, genus-specific primers directed to conserved regions of the Mycobacterium rRNA gene are used to amplify a region of the 16S rRNA gene. Second, identification of particular species of Mycobacterium is performed by hybridizing species-specific probes directed to variable regions of the 16S rRNA gene to the PCR amplification products. Similar methods are disclosed by EP 0 528 306 and P. Kirschner et al. (*J. Clln. Microbiol.* 34, 304–12 (1996)).

Previous methods for detecting Mycobacterium in clinical specimens have suffered from unacceptably high variability in sensitivity, specificity, and incidence of false positives. See, e.g., G. Noordhoek et al., *J. Clin. Microbiol.* 32, 277–84 (1994); G. Pfyffer et al., *J. Clin. Microbiol.* 32, 918–23 (1994). Accordingly, there remains a need in the art for rapid, accurate and sensitive methods of identifying Mycobacteriwn.

SUMMARY OF INVENTION

The present invention provides novel oligonucleotide amplification primers and probes, methods, and kits for genus-specific detection of Mycobacterium nucleic acids.

Accordingly, as a first aspect, the present invention a method for genus-specific detection of Mycobacterium nucleic acids comprising: (a) hybridizing to Mycobacterium nucleic acids an amplification primer comprising nucleotides 25 to 37 of SEQ ID NO:14; (b) amplifying the Mycobacterium nucleic acids; and (c) detecting the amplified Mycobacterium nucleic acids.

As a second aspect, the present invention provides a method for genus-specific detection of Mycobacterium nucleic acids comprising: (a) hybridizing to Mycobacterium nucleic acids a first amplification primer consisting of SEQ ID NO:14 and a second amplification primer consisting of SEQ ID NO:11; (b) amplifying the Mycobacterium nucleic acids; and (c) detecting the amplified Mycobacterium nucleic acids.

As a third aspect, the present invention provides a method for genus-specific detection of Mycobacterium nucleic acids comprising: (a) hybridizing to Mycobacterium nucleic acids a first amplification primer comprising a target binding sequence consisting of nucleotides 25 to 37 of SEQ ID NO:14 and a second amplification primer comprising a target binding region consisting of nucleotides 25 to 39 of SEQ ID NO:11; (b) amplifying the Mycobacterium nucleic acids by extending the hybridized first and second amplification primers; and (c) detecting the amplified Mycobacterium nucleic acids.

As a fourth aspect, the present invention provides a method for genus-specific detection of Mycobacterium nucleic acids, comprising: (a) hybridizing to Mycobacterium nucleic acids a first and a second amplification primer, the first and the second amplification primers each comprising a target binding sequence having a nucleotide sequence selected from the group consisting of nucleotides 25 to 40 of SEQ ID NO:3, nucleotides 25 to 39 of SEQ ID NO:4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, and nucleotides 25 to 37 of SEQ ID NO:14; (b) amplifying the Mycobacterium nucleic acids by extending the hybridized first and second amplification primers; and (c) detecting the amplified Mycobacterium nucleic acids.

As a fifth aspect, the present invention provides a method for genus-specific detection of Mycobacterium nucleic acids comprising: (a) hybridizing a nucleic acid probe to Mycobacterium nucleic acids, the probe having a nucleotide sequence selected from the group consisting of nucleotides 25 to 40 of SEQ ID NO:3, nucleotides 25 to 39 of SEQ ID NO:4, SEQ ID NO:5, SEQ ID NO:6, SEQ ID NO:7, SEQ ID NO:8, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, nucleotides 25 to 37 of SEQ ID NO:14, SEQ ID NO:15, and SEQ ID NO:16; and (b) detecting hybridization between the nucleic acid probe and the Mycobacteriwn nucleic acids.

As a sixth aspect, the present invention provides an oligonucleotide selected from the group consisting of SEQ ID NO:2 to SEQ ID NO:16, nucleotides 25 to 40 of SEQ ID NO:3, nucleotides 25 to 39 of SEQ ID NO:4, nucleotides 25 to 40 of SEQ ID NO: 9, nucleotides 25 to 39 of SEQ ID NO:10, nucleotides 25 to 39 of SEQ ID NO:11, nucleotides 25 to 38 of SEQ NO:12, nucleotides 25 to 37 of SEQ ID NO:13, and nucleotides 25 to 37 of SEQ ID NO:14.

As an seventh aspect, the present invention provides a set of primers for genus-specific amplification of Mycobacterium nucleic acids comprising a first amplification primer comprising nucleotides 25 to 37 of SEQ ID NO:14 or nucleotides 25 to 39 of SEQ ID NO:11.

As a eighth aspect, the present invention provides a set of primers for genus-specific amplification of Mycobacterium nucleic acids comprising an amplification primer consisting of SEQ ID NO:14 or SEQ ID NO:11.

As a ninth aspect, the present invention provides a set of primers for genus-specific amplification of Mycobacterium nucleic acids comprising a first and a second amplification primer, the first and the second amplification primers each comprising a nucleotide sequence selected from the group consisting of nucleotides 25 to 40 of SEQ ID NO:3, nucleotides 25 to 39 of SEQ ID NO:4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, and nucleotides 25 to 37 of SEQ ID NO:14.

Further provided are kits for genus-specific detection of Mycobacterium containing the nucleic acid probes or primer sets disclosed herein.

These and other aspects of the present invention are described in more detail in the description of the invention below.

BRIEF DESCRIPTION OF THE DRAWINGS

FIG. 3 presents the *M. tuberculosis* 16S rRNA gene (MTU16SRNA GenBank accession number 52917) with the target sequences of the Mg733 primer set indicated by labeled boxes.

DETAILED DESCRIPTION OF THE INVENTION

Figure 1:
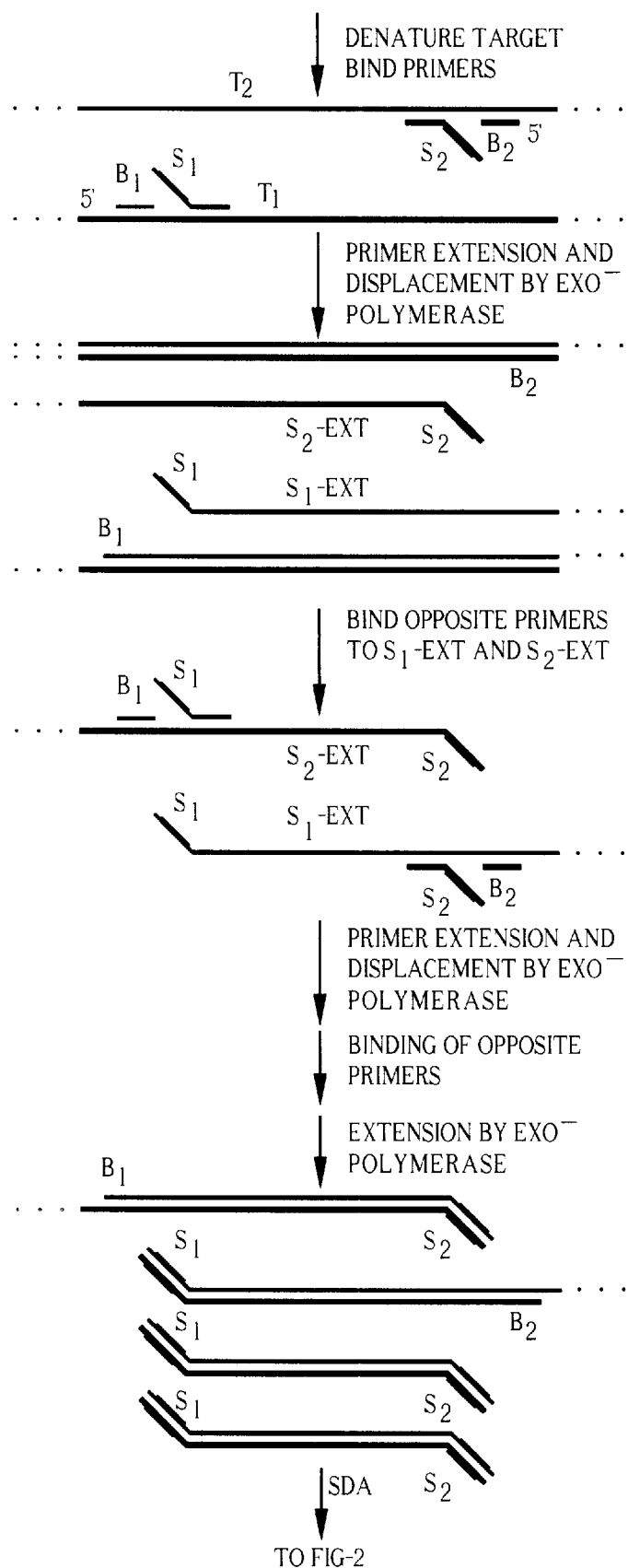
FIG. 1 illustrates the tSDA target generation scheme, modified from G. Walker et al., *Nuc. Acids Res.* 20, 1691 (1992). Sense and antisense DNA strands are shown by thin and thick lines, respectively. The restriction endonuclease recognition sites are shown by raised boxes.

Nucleotide sequences are presented herein by single strand only in the 5' to 3' direction, from left to right. Nucleotides are represented herein in the manner recommended by the IUPAC-IUB Biochemical Nomenclature Commission, in accordance with 37 C.F.R. § 1.822 and established usage.

Disclosed herein are oligonucleotides, methods and kits for genus-specific detection of Mycobacteinum nucleic acids. By "genus-specific" it is meant that the oligonucleotides, methods or kits do not detect non-Mycobacterium nucleic acids under the same conditions in which Mycobacterium nucleic acids are detected. Alternatively stated, the term "genus-specific" refers to detection, amplification or oligonucleotide hybridization in the genus Mycobacterium without substantial detection, amplification or oligonucleotide hybridization in other genuses.

One aspect of the present invention is Mycobacterium-specific amplification primers. An amplification primer is an oligonucleotide for amplification of a target sequence by extension of the oligonucleotide after hybridization to the target sequence or by ligation of multiple oligonucleotides that are adjacent when hybridized to the target sequence. The oligonucleotide primers of the present invention are preferably used to detect Mycobacterium by amplification of Mycobacterium nucleic acid target sequences. However, the portion of the primer that hybridizes to the target sequence (i.e., target binding sequence or annealing region) may also be used as a hybridization probe for direct detection of target Mycobacterium nucleic acids in various nucleic acid hybridization methods, as described in more detail below.

Thus, it will be apparent to those skilled in the art that primers and probes of the present invention in many cases are structurally similar or identical. The terms primer and probe refer to the function of the oligonucleotide. An oligonucleotide may function as a probe if it is hybridized to a target sequence to capture or detect the target sequence. Alternately, the same oligonucleotide may function as a primer if it is used to amplify the target, as described above.

Suitable bases for preparing the oligonucleotide probes or amplification primers of the present invention may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, $\ominus$,D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, $\ominus$,D-mannosylqueosine, 5-methoxycarbonylmethyluridine, 5-methoxyuridine, 2-methylthio-N6-isopentenyladenosine, N-((9-$\ominus$-D-ribofuranosyl-2-methylthiopurine-6-yl)carbamoyl)threonine, N-((9-$\ominus$-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9$\ominus$-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described). The oligonucleotide may be a "peptide nucleic acid" such as described in P. Nielsen et al., *Science* 254, 1497–1500 (1991). The only requirement is that the oligonucleotide probe should possess a sequence at least a portion of which is capable of binding to a portion of the sequence of a target DNA molecule.

Oligonucleotide primers (both amplification and bumper primers) and probes disclosed herein will generally be from about 10, 15, 20 or 25 nucleotides in length to 40, 50 or 75 nucleotides in length. Typically, the total length for a tSDA amplification primer is 20 or 25 nucleotides to 50 or 75 nucleotides.

The amplification primers disclosed herein hybridize to and amplify nucleic acids encoding a portion of the Mycobactelium 16S rRNA. When a set of two or more amplification primers is used to amplify Mycobacterium nucleic acids, it is preferred that the set of amplification primers is contained in a common aqueous solution. In particular embodiments of the present invention, the amplification primers have sequences as given by SEQ ID NO:2 to SEQ ID NO:16. Alternately, the amplification primers or their target binding regions have sequences as given by nucleotides 25 to 40 of SEQ ID NO:3, nucleotides 25 to 39 of SEQ ID NO:4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, or nucleotides 25 to 37 of SEQ ID NO:14. Preferably, the amplification primer has sequence as given by SEQ ID NO:9, SEQ ID NO:10, SEQ ID NO:11, SEQ ID NO:12, SEQ ID NO:13, SEQ ID NO:14, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, or nucleotides 25 to 37 of SEQ ID NO:14. More preferably, the amplification primer has a sequence as given by SEQ ID NO:11, SEQ ID NO:14, nucleotides 25 to 39 of SEQ ID NO:11, or nucleotides 25 to 37 of SEQ ID NO:14. Alternately, in other preferred embodiments, the target binding regions of the amplification primers have sequences as given by nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, or nucleotides 25 to 37 of SEQ ID NO:14. More preferably, the target binding region of the amplification primer has a sequence as given by nucleotides 25 to 39 of SEQ ID NO:11, or nucleotides 25 to 37 of SEQ ID NO:14.

As nucleic acids do not require complete homology to hybridize, it will be apparent to those skilled in the art that the primer sequences specifically disclosed herein may be modified so as to be substantially homologous to the primer sequences disclosed herein without loss of utility as Mycobacterium-specific amplification primers. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

As used herein, the "target sequence" refers to a nucleic acid sequence to which the amplification primer specifically binds and amplifies. These include the original nucleic acid sequence to be amplified and its complementary second strand as well as either strand of a copy of the original target sequence generated during the amplification reaction.

Copies of the target sequence which are generated during the amplification reaction are referred to as "amplification products", "amplimers", or "amplicons". An extension product refers to the copy of a target sequence produced by hybridization of a primer and extension of the primer by polymerase using the target sequence as a template.

The inventive amplification primers disclosed herein can be used in any method of nucleic acid amplification known in the art. Such methods include but are not limited to Polymerase Chain Reaction (PCR; described in U.S. Pat. Nos. 4,683,195, 4,683,202, 4,800,159, 4,965,188), Strand Displacement Amplification (SDA; described by G. Walker et al., *Proc. Nat. Acad. Sci. USA* 89, 392 (1992); G. Walker et al., *Nucl. Acids Res.* 20, 1691 (1992); U.S. Pat. No. 5,270,184, the disclosure of which is hereby incorporated in its entirety by reference), thermophilic Strand Displacement Amplification (tSDA; EP 0 684 315 to Frasier et al.), Self-Sustained Sequence Replication (3SR; J. C. Guatelli et al., *Proc Natl. Acad. Sci. USA* 87, 1874–78 (1990)), Nucleic Acid Sequence-Based Amplification (NASBA; U.S. Pat. No. 5,130,238 to Cangene), the QΘ replicase system (P. Lizardi et al., *BioTechnology* 6, 1197 (1988)), or transcription based amplification (D. Y. Kwoh et al., *Proc. Natl. Acad. Sci. USA* 86, 1173–77 (1989)). Preferably, the amplification primers of the present invention are used to carry out PCR, SDA or tSDA, with tSDA being more preferred.

For amplification by tSDA (or SDA), the oligonucleotide primers are preferably selected such that the GC content is low, preferably less than 70% of the total nucleotide composition of the probe. Similarly, for tSDA the target sequence preferably has a low GC content to minimize secondary structure. An amplification primer for use in tSDA comprises a target binding sequence, a recognition site for a restriction endonuclease, and a tail. The target binding sequence is at the 3' end of the tSDA amplification primer. It hybridizes to the 3' end of the target sequence. The target binding sequence confers hybridization specificity on the amplification primer. A recognition site for a restriction endonuclease is 5' of the target binding sequence. The recognition site is for a restriction endonuclease that will nick one strand of a DNA complex when the recognition site is hemimodified, as described by G. Walker et al. *Proc. Nat'l Acad. Sci. USA* 89, 392 (1992); *Nucl. Acids. Res.* 20, 1691 (1992). The tail of the amplification primer is comprised of nucleotides 5' of the restriction endonuclease recognition site. The tail functions as a polymerase repriming site when the remainder of the amplification primer is nicked and displaced during tSDA. The repriming function of the tail sustains the tSDA reaction and allows synthesis of multiple amplicons from a single target molecule. The length and sequence of the tail region are generally not critical and may be routinely selected and modified to obtain a Tm which will allow the tail to remain hybridized to the target after nicking. One consideration is that the tail should not contain sequences that will hybridize either to the target binding sequence or to other primers.

As used herein, a "bumper primer" or "external primer" is a primer used to displace primer extension products. The bumper primer hybridizes to a target sequence upstream of the amplification primer target binding sequence such that extension of the bumper primer displaces the downstream amplification primer and its extension product. It will not usually be necessary that the bumper primers used in SDA and tSDA reactions be specific to the genus Mycobacterium. The bumper primers are only required to hybridize to their targets upstream from the amplification primers, so that when the bumper primers are extended they will displace the amplification primer and its extension product. The sequence of the bumper primers is therefore generally not critical, and may be derived from any upstream target sequence that is sufficiently close to the binding site of the amplification primer to allow displacement of the amplification primer extension product upon extension of the bumper primer. Occasional mismatches with the target in the bumper primer sequence or some cross-hybridization with non-target sequences do not generally have a negative effect on amplification efficiency as long as the bumper primer still hybridizes to the specific target sequence. Extension of bumper primers is one method for displacing the extension products of amplification primers, but heating is also suitable. In particular embodiments of the present invention, one or more of the bumper primers have sequences as given herein by SEQ ID NO:2, SEQ ID NO:5, SEQ ID NO:7, or SEQ ID NO:8, preferably SEQ ID NO:5, SEQ ID NO:7, or SEQ ID NO:8, more preferably SEQ ID NO:5 or SEQ ID NO:7. Bumper primers may also be used as the target binding sequence of an amplification primer or as a hybridization probe. Bumper primers having sequences given herein as SEQ ID NO:5 and SEQ ID NO:7 are particularly suitable for use as Mycobacterium-specific amplification primers and hybridization probes.

For amplification methods that do not require specialized sequences at the ends of the target (e.g., PCR and LCR), the amplification primer typically consists essentially of only the target binding sequence. For amplification methods other than SDA or tSDA that require specialized sequences in the amplification primer (e.g., an RNA polymerase promoter for 3SR; J. C. Guatelli et al., *Proc Nat. Acad. Sci. USA* 87, 1874–78 (1990), NASBA (U.S. Pat. No. 5,130,238 to Cangene), or transcription based amplification (D. Y. Kwoh et al., *Proc. Natl. Acad. Sci. USA* 86, 1173–77 (1989)), the speciazzed sequence may be linked to the target binding sequence using routine methods for preparation of oligo-nucleotides without altering the hybridization specificity of the target binding sequence.

Another aspect of the present invention is a genus-specific method of detecting Mycobacterium by hybridizing an amplification primer comprising a target binding sequence to Mycobacterium nucleic acids, amplifying the Mycobacteniwm nucleic acids, and then detecting the amplified Mycobacterium nucleic acids. The amplification primers hybridize to, amplify, and detect nucleic acids encoding a portion of the Mycobacteinum 16S rRNA. Typically, the target sequence of the amplification primers will be double-stranded DNA of the Mycobactenim 16S rRNA gene.

Preferably, the inventive methods disclosed herein employ a set of two amplification primers to amplify the Mycobacterium target sequences. Alternately, a single amplification primer or a set of three or more amplification primers can be used to carry out the present invention. Amplification primers for use in carrying out the methods disclosed herein are as described hereinabove.

In one preferred embodiment of the invention, the amplification primers are hybridized to the Mycobacterium nucleic acids and extended. Amplification methods involving extension reactions include but are not limited to PCR, SDA, and tSDA. Any amplification protocol which relies on cyclic, specific hybridization of primers to the target nucleic acid may be used, such as, PCR (described in U.S. Pat. Nos. 4,683,195, 4,683,202, 4,800,159, 4,965,188), SDA (G. Walker et al., *Proc. Nat. Acad. Sci. USA* 89, 392 (1992); G. Walker et al., *Nucl. Acids Res.* 20, 1691 (1992); U.S. Pat. No. 5,270,184, the disclosure of which is hereby incorporated in its entirety by reference), tSDA (EP 0 684 315 to Frasier et al.), 3SR (J. C. Guatelli et al., *Proc Natl. Acad. Sci. USA* 87, 1874–78 (1990)), NASBA (U.S. Pat. No. 5,130,238 to Cangene), the Q$\ominus$ replicase system (P. Lizardi et al., *BioTechnology* 6, 1197 (1988)), or transcription based amplification (D. Y. Kwoh et al., *Proc. Natl. Acad. Sci. USA* 86, 1173–77 (1989)). Amplification by PCR, SDA, and tSDA is preferred, with tSDA being more preferred.

The tSDA reactions can be carried out as described by EP 0 684 315 to Frasier et al. In tSDA reactions, the extension of primers, nicking of a hemi-modified restriction endonuclease recognition site, displacement of single-stranded extension products, annealing of primers to the extension products, and subsequent extension of the primers occurs concurrently in the reaction mix. This is in contrast to PCR, in which the steps of the reaction occur in discrete phases or cycles as a result of the temperature cycling characteristics of the reaction. tSDA is based upon 1) the ability of a restriction endonuclease to nick the unmodified strand of a hemiphosphorothioate form of its double-stranded recognition site, and 2) the ability of certain polymerases to initiate replication at the nick and displace the downstream non-template strand.

Production of each new copy of the target sequence by tSDA consists of five steps: 1) binding of amplification primers to an original target sequence or a displaced single-stranded extension product previously polymerieed, 2) extension of the primers by a 5'–3' exonuclease deficient polymerase incorporating an α-thio deoxynucleoside triphosphate (α-thio dNTP), 3) nicking of a hemi-modified double-stranded restriction site, 4) dissociation of the restriction enzyme from the nick site, and 5) extension from the 3' end of the nick by the 5'–3' exonuclease deficient polymerase with displacement of the downstream newly synthesized strand. Nicking, polymerization and displacement occur concurrently and continuously because extension from the nick regenerates another nickable restriction site. When a pair of amplification primers is used, each of which hybridizes to one of the two strands of a double-stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases that nick their double-stranded recognition sites when an α-thio dNTP is incorporated and that are suitable for tSDA include BsoB1, BsrI, BstNI, BsmAI, BstOI, and BslI.

Figure 2:
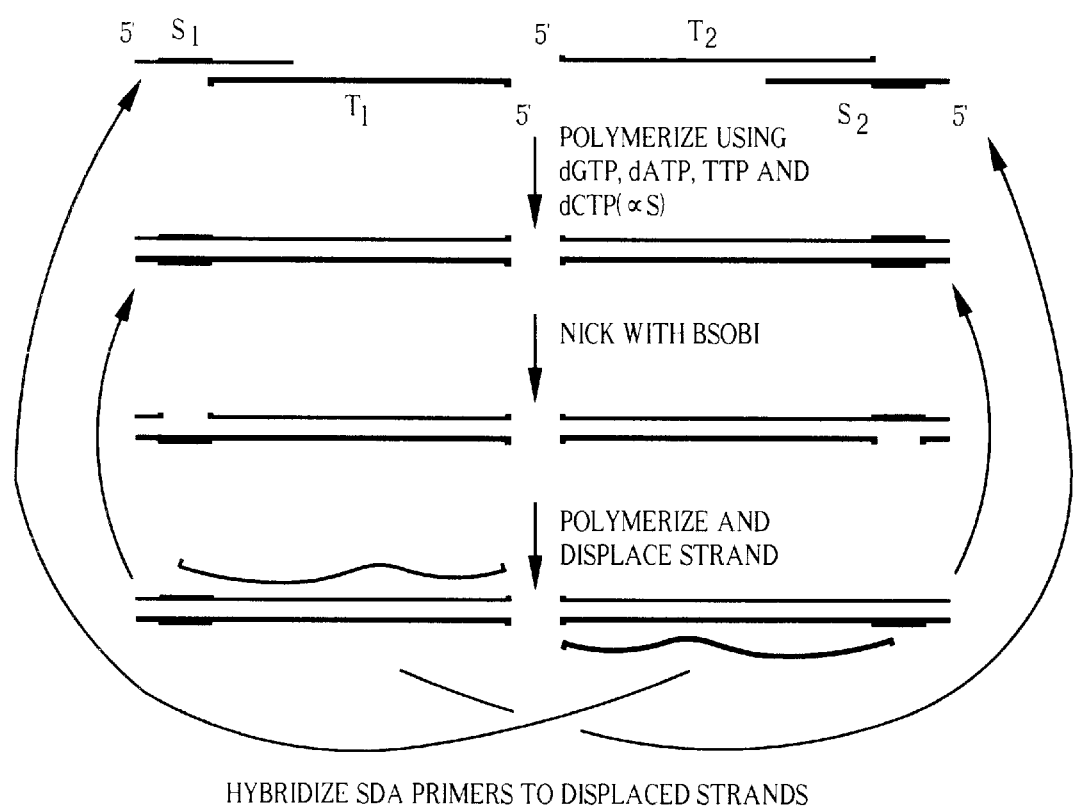
FIG. 2 illustrates the tSDA reaction cycle for a double-stranded target with two amplification primers (exponential amplification), modified from G. Walker et al., *Nuc. Acids Res.* 20, 1691 (1992). The portion of the Figure showing the reaction cycle using only one of the amplification primers illustrates linear amplification. Sense and antisense DNA strands are shown by thin and thick lines, respectively. The restriction endonuclease recognition sites are shown by raised boxes.

The tSDA target generation and amplification reaction schemes are illustrated in FIG. 1 and FIG. 2. Briefly, if the target sequence is double-stranded, the target DNA is heat denatured in the presence of an excess of four primers (B1, B2, S1 and S2). S1 and S2 are amplification primers containing target binding sequences at their 3' ends and a recognition site for a restriction endonuclease (e.g., BsoB1) 5' to the target binding sequences. S1 and S2 bind to opposite strands of double-stranded nucleic acids flanking the target sequence. B1 and B2 bind to the target sequence 5' (i.e., upstream) of the Si and S2, respectively. An exonuclease deficient polymerase (e.g., Bca (Panvera), or Bst (New England BioLabs) is then used to simultaneously extend all four primers in the presence of three deoxynucleoside triphosphates and at least one modified deoxynucleoside triphosphate (e.g., 2'-deoxycytosine 5'-O-(1-thiotriphosphate), "dCTPαS"). The extension products of S1 and S2 are thereby displaced from the original target sequence template by extension of B1 and B2. The displaced, single-stranded extension products of the amplification primers serve as targets for binding of the opposite amplification and bumper primer (e.g., the extension product of SI binds S2 and B2). The next cycle of extension and displacement results in two double-stranded nucleic acid fragments with hemi-modified restriction endonuclease recognition sites at each end. These are suitable substrates for amplification by tSDA. The individual steps of the target generation reaction occur concurrently and continuously, generating target sequences with the recognition sequences at the ends required for nicking by the restriction enzyme in tSDA. As all of the components of the tSDA reaction are already present in the target generation reaction, target sequences generated automatically and continuously enter the tSDA cycle and are amplified.

Amplification reactions employing the primers of the present invention may incorporate thymine as disclosed by G. Walker et al. (*Proc. Nat'l Acad. Sci. USA* 89, 392 (1992); *Nucl. Acids. Res.* 20, 1691 (1992)), or they may wholly or partially substitute 2'-deoxyuridine 5' triphosphate for lTIP in the reaction to reduce cross-contamination with amplification products carried over from previous amplification reactions in reagents, pipetting devices and laboratory surfaces, for example, as is taught in EP 0 624 643. Deoxyuridine (dU) is incorporated into amplification products and can be excised by treatment with uracil DNA glycosylase (UDG). These abasic sites render any contaminating amplification product unamplifiable in subsequent amplification reactions. UDG may be inactivated by UDG inhibitor prior to performing the subsequent amplification to prevent excision of dU in newly-formed amplification products.

The presence of Mycobacterium or Mycobacterium nucleic acids is detected by determining the presence of the amplified Mycobacterium nucleic acids. Amplification products can be detected by hybridization to a labeled probe using conventional techniques. When a probe is used to detect amplification, the probe is typically selected to hybridize to a sequence that lies between the amplification primers (i.e., an internal probe). Alternatively, amplification products may be detected by their characteristic size, for example by electrophoresis followed by ethidium bromide staining to visualize the nucleic acids species. This is the preferred method of detecting amplification products for LCR methods. In a further alternative, a labeled amplification primer is used. In a still further alternative, a labeled amplification primer/internal probe is extended on the target sequence (a detector primer) for detection of amplification products as described by G. Walker et al. *Proc. Nat'l Acad. Sci. USA* 89, 392 (1992); *Nucl. Acids. Res.* 20, 1691 (1992).

Examples of specific detection methods that may be employed to detect amplification productions include a chemiluminescent method in which amplified products are detected using abiotinylated capture probe and an enzyme-conjugated detector probe as described in U.S. Pat. No. 5,470,723. After hybridization of these two probes to different sites of the assay region of the target sequence (i.e., between the binding sites of the two amplification primers), the complex is captured on a streptavidin-coated microtiter plate, and the chemiluminescent signal is developed and read in a luminometer. As a further alternative method, a signal primer as described in EP 0 678 582 is included in the amplification reaction to facilitate detection of the amplification product. According to this embodiment, labeled secondary amplification products are generated during amplification in a target amplification-dependent manner and may be detected as an indication of target amplification by means of the associated label.

Also disclosed herein are nucleic acid hybridization probes. As used herein, the term "probe" indicates an oligonucleotide that hybridizes to a target nucleotide sequence, typically to facilitate its detection. Unlike a primer, a probe is not extended by a polymerase. The probe is often linked to a detectable label to facilitate its detection or capture when hybridized to the target sequence, thus facilitating detection of the target sequence. As used herein, the "target sequence" of a hybridization probe refers to a nucleic acid sequence to which the probe specifically binds. The probes of the present invention find use in various hybridization methods, such as Southern blots for detection of DNA, Northern blots for detection of RNA, and dot blots for detection of either DNA or RNA. These methods are well-known in the art and are described in Sambrook et al., *Molecular Cloning, A Laboratory Manual* (2d ed. 1989)).

The probes disclosed herein hybridize to nucleic acids encoding the Mycobacterium 16S rRNA. In particular embodiments of the invention, the oligonucleotide probe has a sequence as given by nucleotides 25 to 40 of SEQ ID NO:3, nucleotides 25 to 39 of SEQ ID NO:4, SEQ ID NO:5, SEQ ID NO:6, SEQ ID NO:7, SEQ ID NO:8, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, nucleotides 25 to 37 of SEQ ID NO:14, SEQ ID NO:15, or SEQ ID NO:16. As nucleic acids do not require complete homology to hybridize, it will be apparent to those skilled in the art that the probe sequences specifically disclosed herein may be modified so as to be substantially homologous to the probe sequences disclosed herein without loss of utility as Mycobacterium-specific probes. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

Another aspect of the present invention is a genus-specific method for detecting Mycobacterium using a nucleic acid probe. According to this embodiment of the invention, a nucleic acid probe, as described above, is hybridized to Mycobacterium nucleic acids, and the hybridization between the probe and the Mycobacteinum nucleic acids is then detected. Hybridization can be carried out under any suitable technique known in the art. Typically, hybridizations will be performed under conditions of high stringency (e.g., a wash stringency of 0.3 M NaCl, 0.03 M sodium citrate, 0.1% SDS at 60° C. or even 70° C., Sambrook et al., *Molecular Cloning, A Laboratory Manual* (2d ed. 1989)). It will be apparent to those skilled in the art that hybridization conditions can be altered to increase or decrease the degree of hybridization, the level of specificity of the hybridization, and the background level of non-specific binding (i.e., by altering hybridization or wash salt concentrations or temperatures).

Similarly, detection of hybridization between the probe and the Mycobacterium nucleic acids can be carried out by any method known in the art. The probe may contain a detectable label that will indicate hybridization between the labeled probe and the M. kansasii nucleic acids. The detectable label of the probe is a moiety that can be detected either directly or indirectly. For direct detection of the label, probes may be tagged with a radioisotope and detected by autoradiography. Alternatively, the probe may be tagged with a fluorescent moiety and detected by fluorescence as is known in the art. As a further alternative, the probe may be indirectly detected by tagging with a label that requires additional reagents to render it detectable. Illustrative methods of indirect labeling include those utilizing chemiluminescence agents, enzymes that produce visible reaction products, and ligands (e.g., haptens, antibodies or antigens) that may be detected by binding to labeled specific binding partners (e.g., hapten binding to a labeled antibody). Ligand labels are also useful for solid phase capture of the oligonucleotide probe (i.e., capture probes). Exemplary labels include biotin (detectable by binding to labeled avidin or streptavidin) and enzymes, such as horseradish peroxidase or alkine phosphatase (detectable by addition of enzyme substrates to produce a colored reaction product). Methods of labeling oligonucleotides are well known in the art.

The present invention also provides kits for detecting Mycobacterium nucleic acids comprising an oligonucleotide nucleic acid probe or amplification primer, preferably a pair of amplification primers, each as described hereinabove. The kit may additionally contain means for detecting the Mycobacteinum nucleic acids using the oligonucleotide nucleic acid or amplification primer, as described herein above. In an alternate embodiment, the amplification primer contains a sequence for amplification of a target nucleic acid in addition to a target binding sequence, each as described hereinabove. The kit may further include other components and reagents for performing the hybridization or amplification method (e.g., Southern hybridization, dot blot hybridization, PCR, SDA, etc., and the like). As an illustrative example, such a kit may contain at least one pair of amplification primers according to the present invention. For detection by hybridization, a hybridization solution such as 25% formamide, 5X SSC, 5X Denhardt's solution, 100 µg/ml of single stranded DNA, and 5% dextran sulfate, or other reagents known to be useful for probe hybridization may also be included. See Sambrook et al., *Molecular Cloning, A Laboratory Manual* (2d ed. 1989). Alternatively, reagents appropriate for use with one of the known nucleic acid amplification methods may be included with Mycobactenium-specific amplification primers. The components of the kit are packaged together in a common container, typically including instructions for performing selected specific embodiments of the methods disclosed herein. Components for detection methods, as described hereinabove, may optionally be included in the kit, for example, a second probe, and/or reagents and means for performing label detection (e.g., radiolabel, enzyme substrates, antibodies, etc., and the like).

The methods, probes, amplification primers, and kits disclosed herein can be used to detect Mycobacterium in any sample suspected of containing Mycobacterium. The samples may comprise isolated nucleic acids, isolated microorganisms, or they may be clinical samples. Typically, clinical samples are in the form of a biological fluid or tissue (e.g., sputum, bronchial washings, gastric washings, blood, milk, lymph, skin, and soft tissues). As mycobacteria infect both human and non-human animal species, the present invention is applicable to both human and veterinary diagnostic procedures and the sample may be obtained from either source.

The following Examples are provided to illustrate the present invention and should not be construed as limiting thereof. As used herein, "ml" means milliliter, "µl" means microliter, "µM" means micromolar, "mM" means millimolar, "mg" means milligram, "ng" means nanogram, "min." means minute, "sec." means second, "v/v" means volume/volume, "w/v" means weight/volume, "KPO4" means potassium phosphate, "MgAcetate" means magnesium acetate, "DMSO" means dimethylsulfoxide, "EDTA" means ethylenediaminetetraacetic acid, "DTT" means dithiothreitol, "KCl" means potassium chloride, "NaCl" means sodium chloride, and "BSA" means bovine serum albumin.

EXAMPLE 1

Designing Primers for Isothermic Strand Displacement Amplification

A set of Mycobacterium genus-specific primers and bumpers were designed for isothermic Strand Displacement Amplification (SDA) that would amplify a sequence of the 16S rRNA gene of all Mycobacterium species of interest and not amplify nucleic acid sequences in non-Mycobacterium species (i.e., cross-reactants). In addition, it was desired that the primers be able to work in conjunction with primers used for identifying M. tuberculosis by amplification of the IS 6110 region. See, e.g., D. Thierry et al., J. Clin. Microbiol. 28, 2668–73 (1990); Z. Zainuddin et al., J. Gen. Microbiol. 135, 2347–55 (1989).

A computer program, OLIGO-PROBE DESIGN STATION (AGCT Inc., Irvine, Calif.), was used to design SDA primers and bumpers derived from the mycobacterial 16S rRNA gene with the desired characteristics. This program identifies candidate probe sequences from every location of the target gene of interest based on melting temperature (Tm) of the probe. If the target gene is 100 bp, for example, the computer extracts approximately 100 potential probes, one starting from each nucleotide base in the target gene and selects those that satisfy the specified Tm criteria. As Tm represents the actual binding strength of hybridization and stringency of assay conditions, two probes with the same Tm, or similar Tm, can provide high sensitivity and selectivity as a primer pair.

Each candidate probe was analyzed for potential hybridization against sequences in the GenBank Bacterial Database using an algorithm for homology analysis. In a homology calculation for mismatched probes, the program calculated Tm at the longest non-mismatched stretch of nucleotide sequences. This screening process identified all sequences in the database that may hybridize to each candidate probe. From these data, probe sequences having identity to 16S rRNA sequences from the Mycobacterium species of interest were identified.

Probe sequences showing identity with numerous species of Mycobacterium were then screened for cross-reactivity with non-Mycobacterium species. The screening strategy consisted of comparing the probe sequences against sequences in the GenBank Bacterial Database and against sequences in smaller databases containing only genes from suspected cross-reactant species. From these screenings, probes were selected that should hybridize to all of the Mycobacterium species of interest, but not to any non-Mycobacterium sequences.

EXAMPLE 2

Candidate Primer and Bumpers

Based on the screening strategy described in Example 1, a set of SDA primers and bumpers were designed by AGCT Inc. as shown below. The amplification primers (designated Sg 7.0 and Sg 7.1) had sequences as given in SEQ ID NO:3 and SEQ ID NO:4, and the bumpers (designated Bg 7.0 and Bg 7.1) had sequences as given in SEQ ID NO:2 and SEQ ID NO:5. The probes identified in Example 1 form the annealing regions (i.e., target binding sequences) of the amplification primers (underlined below), given by nucleotides 25 to 40 of SEQ ID NO:3 (Sg 7.0) and nucleotides 25 to 39 of SEQ ID NO:4 (Sg 7.1).

The target binding region of Sg 7.0 is complementary to nucleotides 942 to 957 of the M. tuberculois 16S rRNA gene (MTU16SRNA GenBank accession number 52917; SEQ ID NO:1, FIG. 3). The target binding region of Sg 7.1 is complementary to nucleotides 988 to 1001 on the (-) strand of the M. tuberculosis rRNA gene. The amplification primers also contain a recognition site for the endonuclease Hinc II (GTTGAC) at nucleotides 19 to 24 of SEQ ID NO:3 and SEQ ID NO:4 (italicized below). The remaining portion of the primers (nucleotides 1 to 18 of SEQ ID NO:3 and SEQ ID NO:4) constitute the tail region.

As shown in FIG. 3, this Hinc II SDA primer set targets a 99 bp fragment of the 16S rRNA gene from nucleotide 922 to nucleotide 1020 of the M. tuberculosis 16S rRNA gene (SEQ ID NO:1).

A further oligonucleotide detection probe (SEQ ID NO:6) was designed to detect the amplified products. This probe was 5'-32P-labeled using T4 polykinase radiolabel extension reactions as described below in Example 5. Alternatively, amplification products were detected using a biotin-capture alkline phosphatase detection assay.

Bg7.0: complementary to nt 922–935 of the M. tuberculosis rRNA gene

ACGCGAAGAA CCTT                                    SEQ ID NO:2

Sg7.0: complementary to nt 942–957 of the *M. tuberculosis* rRNA gene

AACTTAGTAC GGAATCAAG TTGACGTTTG ACATGCACAG G                                                SEQ ID NO:3

Sg7.1: complementary to nt 988–1001 of the (-) strand of the *M. tuberculosis* rRNA gene TTCATCTTGA GCTTGTATGT TGACGCACCT GCACACAGG                                      SEQ ID NO:4

Bg7.1: complementary to nt 1007–1020 of the (-) strand of the *M. tuberculosis* rRNA gene

GCTGACGACA GCCA                                    SEQ ID NO:5

Dg70.2: complementary to nt 974–987 of the *M. tuberculosis* rRNA gene

GCGTTCCCTT GTGG SEQ ID NO:6

EXAMPLE 3

Protocol for Isothernic Strand Displacement Amplification

Isothermic SDA reactions were generally performed as previously described (Walker et al., *Nucl. Acids Res.* 20, 1691–96 (1992)), with substitution of dUTP for TTP to allow for inactivation (decontamination) of amplicons carried over to subsequent reactions using uracil DNA glycosylase (UDG), as described in EP 0 624 643.

The SDA reaction was carried out in microfuge tubes in a final reaction volume of 50 µl. Reaction mix (37.5 µl) was transferred to each reaction tube (reaction mix=58.7 mM KP04, 0.13 mg/ml BSA, 0.27 mM α-thio-dATP, dCTP, and dGTP, 0.67 mM dUTP, 0.67 µM of each amplification primer (SEQ ID NO:3 and SEQ ID NO:4), 0.067 µM of each bumper oligonucleotide (SEQ ID NO:2 and SEQ ID NO:5), 13.33 % (v/v) DMSO, and 6.67% (v/v) glycerol). Approximately 106 genomes of template DNA (5 µl of 0.84 ng/µl stock solution diluted in 10 ng/µl human placental DNA) was added to give a final concentration of 0.1 ng/µl.

Template DNA was denatured by boiling the samples for 2 minutes. The reaction tubes were transferred to a Thermallok (USA Scientific, Ocala, Fla.) and allowed to equilibrate for 2 minutes.

To prevent contamination by previous amplification products, the samples were treated with uracil DNA glycosylase (UDG) prior to amplification, as described in EP 0 624 643. The UDG treatment will remove uracil intentionally incorporated into previously amplified nucleic acids, thereby rendering the uracil-containing DNA unamplifiable in subsequent PCR reactions. One microliter of UDG enzyme (stock=1 unit/µl in 50% (v/v) glycerol, 150 mM NaCl, 30 mM Tris.HCl, pH 7.5, 1 mM EDTA, 1 mM DTT) was added to each reaction tube. The decontamination reaction was left for 30 minutes at the same temperature as for the amplification reaction (typically 39–41° C., preferably 41° C.).

The SDA reactions were started by adding an SDA enzyme mix (6.5 il) containing 150 units of Hinc II (stock solution=75 units/µl in 50% (v/v) glycerol, 50 mM KCl, 10 mM Tris.HCl, pH 7.4, 1 mM DTT, 200 µg/ml acetylated BSA), 6 units exo- Klenow fragment (exonuclease deficient large fragment of *E. coli* DNA polymerase I from New England Biolabs; stock=6 units/µl in 50% (v/v) glycerol, 50 mM KPO4, 1 mM DTT), and 2 units uridine DNA glycosylase inhibitor (UDI; stock=2 units/L in 50% (v/v) glycerol, 150 mM NaCl, 30 mM Tris.HCI, pH 7.5, 1 mM EDTA, 1 mM DTT) in a 31 mM MgAcetate buffer.

The final reaction conditions (final volume=50 µl) were: 45 mM KPO4, 0.1 mg/ml BSA, 0.2 mM α-thio-dATP, dCTP, and dGTP, 0.5 mM dUTP, 0.5 µM each amplification primer (SEQ ID NO:3 and SEQ ID NO:4), 0.05 µM each bumper oligonucleotide (SEQ ID NO:2 and SEQ ID NO:5), 10% (v/v) DMSO, 10% (v/v) glycerol, 1 unit UDG, 4 mM MgAcetate, 150 units Hinc II, 6 units exo- Klenow polymerase, 2 units UDI, and 0.084 ng/µl template DNA.

The reactions were incubated for 2 hours at 39–41° C. for optimization experiments, and at 41° C. thereafter. The reactions were stopped by boiling the samples for 2 minutes. Samples were stored at –20° C. until analysis. Amplification products were analyzed by radiolabel extension assays as described in Example 5.

EXAMPLE 4

Optmizing Conditions for Strand Displacement Amplification

The standard protocol for the isothermic SDA reactions is as described above in Example 3. The conditions for carrying out the SDA reactions with the amplification primers and bumpers described in Example 2 were optimized by using S-plus Statistical Experimental Design (MathSoft, Inc., Seattle, WA). Using this technique, a variety of salt and solvent conditions were quickly screened, and an optimal SDA system was developed for the primer set of Example 2.

The ranges of temperature, salt, and solvent conditions tested were as follows:

39–41° C.
37.5–57.5 mM KPO4
2–8 mM MgAcetate
5–35% (v/v) glycerol
0–20% (v/v) DMSO Some SDA product was observed in all of the conditions tested in the ranges described above, but the best SDA conditions were: 41° C., 45 mM KPO4, 4 mM MgAcetate, 10% (v/v) glycerol, and 10% (v/v) DMSO.

EXAMPLE 5

Radiolabel Extension Reactions

The detection probes were 5'-32P-labeled using T4 polykinase to facilitate detection of amplification product. The radiolabeling conditions were: 1 mM detector probe oligonucleotide, 30 units T4 DNA polynucleotide kinase, 70 µCi γ-32P-ATP, and 1X PNK buffer (10X PNK buffer available from USB). The reactions were allowed to proceed at 37° C. for 45 minutes, and were stopped by heating the samples at 65° C. for 10 minutes. The labeled detection probe was stored at –20° C. and used within one week.

The radiolabel extension reactions were carried out by mixing 5 μl of the tSDA sample with 5 μl of the detection mix containing the radiolabeled detection probe (detection mix=(50 mM KP)4, 0.2 mM each α-thio-dATP, dCTP, and dGTP, 0.5 mM dUTP, and 1 μl radiolabeled detection probe). The samples were boiled for 2 minutes, followed by at least 2 minutes of equilibration in a 37° C. waterbath. Enzyme mix (1 μl) was added to each detection reaction and incubated at 37° C. for 10 minutes (enzyme mix=2 units exo-Klenow and 1X React 1 buffer (10X React 1 buffer available from BRL Life Technologies Inc.). Reactions were stopped by the addition of 10 μl stop mix (available from USB; 3X=95% formamide, 20 mM EDTA, 0.05% bromophenol blue, 0.05% xylene cyanol), followed by boiling the samples for 2 minutes. Radiolabeled extension products were detected by separating the reaction products through an 8% polyacrylamide gel followed by autoradiography and quantification with a Molecular Dynamics 455SI phosphoimager and ImageQuant v1.1 software.

EXAMPLE 6

Sensitivity and Specificity of the SDA Priner Set

Under the optimized SDA conditions described in Example 4, a sensitivity of 100 genomes for *M. tuberculosis* and at least 1000 genomes for all other Mycobacterium tested was achieved with the SDA primer set described in Example 2. Of the 18 non-Mycobacterium species tested for cross-reactivity, none were detected at a concentration of 1,000,000 genomes by conventional SDA using the SDA primer set.

EXAMPLE 7

Protocol for Thernophilic Strand Displacement Amplification

The tSDA reactions were carried out essentially as previously described in EP 0 684 315 to Frasier et al., with substitution of dUTP for ITP to allow for inactivation (decontamination) of amplicons carried over to subsequent reactions using uracil DNA glycosylase (UDG).

For each tSDA reaction, 40 μl reaction mix was transferred to each reaction tube (reaction mix=31.2 mM KPO4, 0.019% (v/v) antifoam, 6.25% (v/v) DMSO, 1.75 mM α-thio-dCTP, 0.62 mM dUTP, 0.25 mM dGTP, and 0.25 mM dATP, 0.62 μM each amplification primer, 0.06 μM each bumper oligonucleotide, 125 μg/ml BSA, 500 ng human placental DNA, 0.45 mM DTT, 2.28% (v/v) trehalose, and 6.25 mM MgAcetate). Approximately 106 genomes of template DNA (5 μl of 0.84 ng/μl stock solution diluted in 10 ng/μl human placental DNA) were added to each reaction tube.

DNA was denatured by boiling the samples for 2 minutes. The reaction tubes were transferred to a Thermal-lok and allowed to equilibrate for 2 minutes.

To prevent contamination by previous amplification products, the samples were treated with uracil DNA glycosylase (UDG) prior to amplification, as described in EP 0 624 643. The UDG treatment removes uracil intentionally incorporated uracil into previously amplified nucleic acids, thereby rendering the uracil-containing DNA unamplifiable in subsequent PCR reactions. One microliter of UDG enzyme (stock=1 unit/μl in 50% (v/v) glycerol, 150 mM NaCl, 30 mM Tris.HCl, pH 7.5, 1 mM EDTA, 1 mM DTT) was added to each reaction tube. The decontamination reaction was left at 41° C. for 30 minutes. The samples were then transferred to a Thermal-lok set at 65° C. for 10 minutes.

The tSDA reactions were started by addition of a tSDA enzyme mix (4 μl) containing: 160 units BsoBl (supplied by New England Biolabs; stock solution=160,000 units/ml in 50% glycerol), 12.5 units of Bst1 polymerase (an exonuclease deficient DNA polymerase I, purchased from New England BioLabs; stock solution=120,000 units/ml in 50% glycerol), 2 units uridine DNA glycosylase inhibitor (UDI; stock=2 units/μl in a buffer of 50% (v/v) glycerol, 150 mM NaCl, 30 mM Tris.HCl, pH 7.5, 1 mM EDTA, 1 mM DTT), and 26% (v/v) glycerol.

The final reaction conditions (final volume=50 μl) were: 25 mM KPO4, 0.015% (w/v) antifoam, 5% (v/v) DMSO, 1.4 mM α-thio-dCTP, 0.5 mM dUTP, 0.2 mM dGTP, and 0.2 mM DATP, 0.5 mM each amplification primer, 0.05 mM each bumper oligonucleotide, 100 μg/ml BSA, 550 ng human placental DNA, 0.36 mM DTT, 1.82% (w/v) trehalose, 5 mM MgAcetate, 1 unit UDG, 5.15% (v/v) glycerol, 160 units BsoB1, 12.5 units Bst1 polymerase, 2 units UDI, and 0.084 ng/μl template DNA.

The reactions were incubated at 52.6° C. in a Thermal-lok for 30 minutes. The reactions were stopped by boiling samples for 5 minutes. Samples are stored at −20° C. until analysis.

EXAMPLE 8

Modification of Primer Set for Thermophilic Strand Displacement Amplification The Hinc II SDA primer set described in Example 2 was converted for use in thermophilic Strand Displacement Amplification (tSDA). This process consisted of redesigning the restriction site (i.e., converting the Hinc II recognition sequence to a BsoBl recognition sequence) and tail of the amplification primers, adjusting the length (and consequently the Tm) of the annealing region (i.e., target binding region) of the primers, as well as the length and Tm of the bumpers.

The amplification and bumper primers tested are as shown below. The BsoBl recognition sites (CTCGGG) are italicized and the target binding sequences are underlined.

1. Bumpers

Mg7.BL     15mer     Tm 44° C.    nt922 - 936    (Bg7.0 + 1 bp at 3' end)
        ACGCG AAGAA CCTTA                            SEQ ID NO:7

Mg7.BR     14mer     Tm 44° C.    nt1020 - 1007
        GCTGA CGACA GCAA                             SEQ ID NO:8

Mg7.BR2    14mer     Tm 48° C.    nt1020 - 1007  (Bg7.1)
        GCTGA CGACA GCCA                             SEQ ID NO:5

2. Amplification Primers

Mg7.AL1    40mer     Tm 48° C.    nt942 - 957    (Sg7.0)
    CGATTCCGCT CCAGACTT*CT CGGGG*GTTTGA CATGCACAGG   SEQ ID NO:9

Mg7.AL2    39mer     Tm 44° C.    nt943 - 957    (1 bp removed 5')
    CGATTCCGCT CCAGACTT*CT CGGG*TTTGAC ATGCACAGGG    SEQ ID NO:10

Mg7.AL3    39mer     Tm 44° C.    nt942 - 956    (1 bp removed 3')
    CGATTCCGCT CCAGACTT*CT CGGGG*GTTTGA CATGCACAG    SEQ ID NO:11

Mg7.AR1    38mer     Tm 46° C.    nt1001 - 988   (Sg7.1)
    ACCGCATCGA ATGCATGT*CT CGGG*CACCTG CACACAGG      SEQ ID NO:12

Mg7.AR2    37mer     Tm 42° C.    nt1000 - 988   (1 bp removed 5')
    ACCGCATCGA ATGCATGT*CT CGGG*ACCTGC ACACAGG       SEQ ID NO:13

Mg7.AR3    37mer     Tm 42° C.    nt1001 - 989   (1 bp removed 3')
    ACCGCATCGA ATGCATGT*CT CGGG*CACCTG CACACAG       SEQ ID NO:14

3. Detection Probes

Mg7.D1L    15mer     Tm 46° C.    nt973 - 987
        GGCGT TCCCT TGTGG                            SEQ ID NO:15

Mg7.D1R    15mer     Tm 46° C.    nt987 - 973    (opposite strand)
        CCACA AGGGA ACGCC                            SEQ ID NO:16

4. Summary (FIG. 3)
Target region within the 16S rRNA gene:      nt 922 - 1020
Bumper - Amplification primer distances:     5 bp
Bumper - Bumper region:                      99 bp
Amplification region (restriction site)      70 bp
Assay region (3? primers)                    32 bp

EXAMPLE 9

Screening Primers for Thermophific Strand Displacement Amplification

An experiment was performed to determine which combination of amplification primers and bumpers from Example 8 produced the greatest amplification by tSDA under the test conditions, at a set temperature of 52.6° C. The amplifications were carried out essentially as described in Example 7, but with varying concentrations of human placental DNA, KPO4 and MgAcetate, and without the addition of antifoam, DTT, trehalose, or the hot start incubation. All amplification reactions included both BL (left) and BR (right) bumpers. All possible combinations of amplification primers were tested (i.e., Mg7.AL1 with Mg7.AR1, Mg7.AL1 with Mg7.AR2, Mg7.AL1 with Mg7.AR3, etc.). Other reaction conditions were 5% (v/v) glycerol, 5% (v/v) DMSO, 160 units BsoB1, and 12.5 units BstI polymerase. The variable factors were tested in a statistically designed matrix of the following four combinations:

|  | hDNA | KPO4 | MgAcetate |
| --- | --- | --- | --- |
| condition 1 | 300 ng | 25 mM | 6.7 mM |
| condition 2 | 1050 ng | 25 mM | 5.7 mM |
| condition 3 | 300 ng | 35 mM | 5.7 mM |
| condition 4 | 1050 ng | 35 mM | 6.7 mM |

The target DNA was *M. tuberculosis* H37Rv chromosomal DNA at a concentration of 105 genomes/test reaction. Amplified product was detected in a radiolabel extension reaction using the probe Mg7.DlR (SEQ ID NO:16) as described in Example 5, and quantification was performed with a Molecular Dynamics 455SI phosphoimager and InageQuant v1.1 software.

All primer combinations amplified specific product under condition 3 above (i.e., 300 ng human placental DNA, 35 mM KPO4, and 5.7 mM MgAcetate). However, the primer combination of Mg7.AL3 (SEQ ID NO:11) and Mg7.AR3 (SEQ ID NO:14) amplified the largest amount of product under the four conditions tested. This primer combination, along with the Mg7.BL (SEQ ID NO:7) and Mg7.BR (SEQ ID NO:8) bumpers, made up the primer set designated Mg733.

EXAMPLE 10

Optimization of Reaction Conditions for Thermophilic Strand Displacement Amplification Development of the Mg733 primer set was continued by carrying out a series of S-Plus statistical design experiments to optimize the concentrations of co-solvents, MgAcetate, KPO4, and human placental DNA. The addition of antifoam, DTT, trehalose, and a hot start incubation was included within the testing conditions. During these experiments, the bumper Mg7.BR2 (SEQ ID NO:5) was substituted for Mg7.BR (SEQ ID NO:8). Amplification products were detected by radiolabel extension using detection probe Mg7.D1L (SEQ ID NO:15), which gave greater intensities on the phosphoimager screens and autoradiographs as compared with radiolabel extension reactions performed with the detection probe Mg7.D1R (SEQ ID NO:16).

Amplification from *M. tuberculosis* H37Rv genomic DNA using the Mg733 primer set was possible in the following ranges of reaction conditions. These ranges only indicate the conditions tested; the primer set can still amplify under conditions outside of those specifically tested. The tested ranges were:

| | |
|---|---|
| KPO4 | 20–40 mM |
| DMSO | 3–10% (v/v) |
| Glycerol | 5–10% (v/v) |
| MgAcetate | 5–8 mM |
| hDNA | 300–2000 ng |

The conditions identified as producing the greatest amplification were: 52.6° C., 30.5 mM KPO4, 5 mM MgAcetate, 5.15% (v/v) glycerol, 6% (v/v) DMSO, 683 ng human placental DNA, 160 units BsoB1, and 12.5 units Bst1 polymerase.

EXAMPLE 11

Sequence Alignment of the tSDA Primer Set Mg733

The Mg733 target binding sequence was aligned with DNA sequences of the 16S rRNA genes of Mycobacterium species from GenBank. Out of 114 species of Mycobacterium examined, only 2 species were predicted to be unamplifiable with the Mg733 primer set (including Mg7.BR2; SEQ ID NO:5) due to mismatches or extra bases inserted into the reported sequence for these two strains in the primer annealing regions. These two species are shown below:

*M. aurum*
BL: 0 mismatches    AL3: 9 mismatches    AR3: 26 mismatches  BR2: 1 mismatch
*M. chitae*
BL: 1 mismatch      AL3: 3 mismatches    AR3: 22 mismatches  BR2: 0 mismatches The primer annealing regions of the Mg733 primers and bumpers were also aligned with the 16S rRNA gene sequences from 67 suspected cross-reactant non-Mycobacterium species. Only 3 of the species examined had less than 3 mismatches in any primer annealing region. These species, all from the genus Nocardia, are shown below.

*Nocardia asteroides*
BL: 0 mismatches    AL3: 2 mismatches    AR3: 2 mismatches    BR2: 0 mismatches
*Nocardia asteroides*
BL: 0 mismatches    AL3: 2 mismatches    AR3: 2 mismatches    BR2: 0 mismatches
*Nocardia asteroides*
BL: 0 mismatches    AL3: 2 mismatches    AR3: 2 mismatches    BR2: 0 mismatches In practice, as shown below in Example 14, none of these potential cross-reactant species were amplified or detected by the Mg733 primer set.

EXAMPLE 12

Sensitivity of tSDA Primer Set Mg733

Under the optimized tSDA conditions as described in Example 10, the sensitivity of the Mg733 system was evaluated by carrying out a titration of *M. tuberculosis* H37Rv genomic DNA from $10^4$ genomes to $10^0$ (i.e., 1) genome. The results are shown in Table 1. These data demonstrate that the Mg733 primer set can consistently detect 10 genomes of template DNA (3/3 replicates), and can detect as little as 1 genome (1/3 replicates at a level 2-fold above background).

TABLE 1

Titration of *M. tuberculosis* H37Rv DNA

| GENOMES | INTENSITY OF PRODUCT |
|---|---|
| $10^4$ | 17,337,557 |
| $10^3$ | 2,357,563 |
| $10^3$ | 4,456,533 |
| $10^2$ | 413,908 |
| $10^2$ | 174,161 |
| $10^2$ | 174,134 |
| $10^1$ | 102,904 |
| $10^1$ | 60,732 |
| $10^1$ | 76,549 |
| $10^0$ | 43,134 |
| $10^0$ | 122,711 |
| $10^0$ | 52,310 |
| 0 | 38,867 |

EXAMPLE 13

Mycobacterium Specificity of the Mg733 Primer Set

To determine if the Mg733 primer set can amplify the the Mycobacterium species of medical interest, chromosomal DNA preparations from numerous species of Mycobacterium were tested at a nominal concentration of 10² genomes/amplification reaction. Amplification were carried out under the preferred tSDA reaction conditions as described in Example 10.

The results are presented below in Table 2. All of the Mycobacterium species of interest were amplified and detected by the Mg733 primer set.

TABLE 2

Specificity of the Mg733 Primer Set for the Genus Mycobacterium

| Species | Strain ID | Amplification |
| --- | --- | --- |
| M. africanum | 35711 | +ve |
| M. avium | 25291 | +ve |
| M. bovis BCG | CDC4 | +ve |
| M. chelonae | 1543 | +ve |
| M. flavescens | 2601 | +ve |
| M. fortuitum | 2808 | +ve |
| M. gastri | 1301 | +ve |
| M. genevense | PIR45 | +ve |
| M. gordonae | 13118 | +ve |
| M. haemophilum | 27548 | +ve |
| M. intracellulare | 13950 | +ve |
| M. kansasii | 1201 | +ve |
| M. kansasii | 10892 | +ve |
| M. malmoense | 29511 | +ve |
| M. marinum | 801 | +ve |
| M. microti | 203 | +ve |
| M. phlei | 11758 | +ve |
| M. paratuberculosis | Linda | +ve |
| M. scrofulaceum | 1302 | +ve |
| M. simiae | CDC2 | +ve |
| M. smegmatis | 19420 | +ve |
| M. szulgae | 1328 | +ve |
| M. terrae | 3010 | +ve |
| M. tuberculosis | H37Rv | +ve |
| M. ulcerans | 19423 | +ve |
| M. xenopi | 1901 | +ve |

EXAMPLE 14

Specificity of the Mg733 Primer Set—Cross-reactivity Studies

To determine whether the Mg733 primer set amplifies and detects any of the common bacterial species found in sputum samples, the potential cross-reactant species were tested at 10⁷ genomes in amplification reactions performed under the preferred reaction conditions, as described in Example 10.

These suspected cross-reactants were tested in pooled samples of three species, with a control of the same pool spiked with 10³ genomes of M. tuberculosis H37Rv genomic DNA to show that each pool was not inhibiting amplification, thereby giving a false negative result. Where necessary, pools were split and the constituent species were tested individually.

The results are presented in Table 3. None of the suspected cross-reactant species in fact showed any cross-reactivity with the Mg733 primer set.

TABLE 3

Cross-Reactivity of the Mg733 Primer Set with non-Mycobacterium DNA

| Species | Strain ID | Amplification |
| --- | --- | --- |
| Actinomyces israelli | 10049 | −ve |
| Actinoplanes auranticlor | 15330 | −ve |
| Corynebacterium diptheriae | 11913 | −ve |
| Corynebacterium pseudodiptheriae | 10700 | −ve |
| Corynebacterium xerosis | 373 | −ve |
| Eubacterium lentum | 43055 | −ve |
| Nocardia brasiliensis | 19296 | −ve |
| Nocardia asteroides | 3308 | −ve |
| Nocardia orientalis | 19795 | −ve |
| Propionobacterium acnes | 6919 | −ve |
| Rhodococcus equi | 6939 | −ve |
| Rhodococcus rhodocrous | 13808 | −ve |
| Streptomyces albus | 3004 | −ve |
| Streptomyces gedanensis | 4880 | −ve |
| Streptomyces griseus | 10137 | −ve |
| Streptomyces somaliensis | 13201 | −ve |
| Streptomyces viridialbum | 33328 | −ve |
| Streptomyces alboverticilatum | 29818 | −ve |

What is claimed is:

1. A method for genus-specific detection of Mycobacterium nucleic acids comprising:
   (a) hybridizing to Mycobacterium nucleic acids an amplification primer comprising nucleotides 25 to 37 of SEQ ID NO:14;
   (b) amplifying said Mycobacterium nucleic acids; and
   (c) detecting the amplified Mycobacterium nucleic acids.

2. A method according to claim 1, where said amplification primer consists of SEQ ID NO:14.

3. A method according to claim 1, wherein said Mycobacterium nucleic acids are amplified by extending the hybridized amplification primer.

4. A method according to claim 1, further comprising hybridizing a second amplification primer comprising nucleotides 25 to 39 of SEQ ID NO:11 to said Mycobacterium nucleic acids.

5. A method according to claim 4, where said second amplification primer consists of SEQ ID NO:11.

6. A method according to claim 4, further comprising hybridizing a first and a second bumper primer to said Mycobacterium nucleic acids, said first bumper primer comprising SEQ ID NO:7 and said second bumper primer comprising a sequence selected from the group consisting of SEQ ID NO:5 and SEQ ID NO:8.

7. A method for genus-pecific detection of Mycobacterium nucleic acids comprising:
   (a) hybridizing to Mycobacterium nucleic acids a first amplification primer onsisting of SEQ ID NO:14 and a second amplification primer consisting of SEQ ID NO:11;
   (b) amplifying said Mycobacterium nucleic acids; and
   (c) detecting the amplified Mycobacterium nucleic acids.

8. A method according to claim 7, wherein said Mycobacterium nucleic acids are amplified by extending the hybridized first and second amplification primers.

9. A method according to claim 8, further comprising hybridizing a first and a second bumper primer to said Mycobacterium nucleic acids, said first bumper primer comprising SEQ ID NO:7 and said second bumper primer comprising a sequence selected from the group consisting of SEQ ID NO:5 and SEQ ID NO:8.

10. A method for genus-specific detection of Mycobacterium nucleic acids comprising:
    (a) hybridizing to Mycobacterium nucleic acids a first amplification primer comprising a target binding sequence consisting of nucleotides 25 to 37 of SEQ ID NO:14 and a second amplification primer comprising a target binding region consisting of nucleotides 25 to 39 of SEQ ID NO:11;
    (b) amplifying said Mycobacterium nucleic acids by extending the hybridized first and second amplification primers; and
    (c) detecting the amplified Mycobacterium nucleic acids.

11. A method according to claim 10, where said first amplification primer consists of SEQ ID NO:14 and said second amplification primer consists of SEQ ID NO:11.

12. A method according to claim 10, further comprising hybridizing a first and a second bumper primer to said Mycobacterium nucleic acids, said first bumper primer comprising SEQ ID NO:7 and said second bumper primer comprising a sequence selected from the group consisting of SEQ ID NO:5 and SEQ ID NO:8.

13. A method according to claim 10 where said amplified Mycobacterium nucleic acids are detected using a radiolabeled detection probe.

14. A method according to claim 13, where said detection probe consists of a sequence selected from the group consisting of SEQ ID NO:15 and SEQ ID NO:16.

15. A method for genus-specific detection of Mycobacterium nucleic acids, comprising:
    (a) hybridizing to Mycobacterium nucleic acids a first and a second amplification primer, said first and second amplification primers each comprising a target binding sequence wherein the said target binding sequence of said first amplification primer consists of a nucleotide sequence selected from the group consisting of nucleotides 25–40 of SEQ ID NO:3, nucleotides 25–39 of SEQ ID NO:4, nucleotides 25–40 of SEQ ID NO:9, nucleotides 25–39 of SEQ ID NO:10, nucleotides 25–39 of SEQ ID NO:11, nucleotides 25–38 of SEQ ID NO:12, nucleotides 25–37 of SEQ ID NO:13, and nucleotides 25–37 of SEQ ID NO:14; and wherein the said target binding sequence of said second amplification primer consists of a sequence selected from the group consisting of: nucleotides 25–40 of SEQ ID NO:3, nucleotides 25–39 of SEQ ID NO:4, nucleotides 25–40 of SEQ ID NO:9, nucleotides 25–39 of SEQ ID NO:10, nucleotides 25–39 of SEQ ID NO:11, nucleotides 25–38 of SEQ ID NO:12, nucleotides 25–37 of SEQ ID NO:13, and nucleotides 25–37 of SEQ ID NO:14;
    (b) amplifying said Mycobacterium nucleic acids by extending the hybridized first and second amplification primers; and
    (c) detecting the amplified Mycobacterium nucleic acids.

16. A method according to claim 15, where said amplification primer includes a specilized sequence required for amplification of the target nucleic acids.

17. An oligonucleotide consisting of a sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, nucleotides 25–40 of SEQ ID NO:3, nucleotides 25–39 of SEQ ID NO:4, nucleotides 25–40 of SEQ ID NO:9, nucleotides 25–39 of SEQ ID NO:10, nucleotides 25–39 of SEQ ID NO:11, nucleotides 25–38 of SEQ ID NO:12, nucleotides 25–37 of SEQ ID NO:13, and nucleotides 25–37 of SEQ ID NO:14.

18. An amplification primer comprising at most 75 nucleotides and a target binding sequence selected from the group consisting of nucleotides 25 to 40 of SEQ ID NO:3, nucleotides 25 to 39 of SEQ ID NO :4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, and nucleotides 25 to 37 of SEQ ID NO:14.

19. An amplification primer according to claim 18 wherein said primer consists of a nucleotide sequence selected from the group consisting of SEQ ID NO:3, SEQ ID NO:4, SEQ ID NO:9, SEQ ID NO:10, SEQ ID NO:11, SEQ ID NO:12, SEQ ID NO:13, and SEQ ID NO:14.

20. A set of primers for genus-specific amplification of Mycobacterium nucleic acids consisting of a first amplfication primer consisting of SEQ ID NO:14 and a second amplification primer consisting of SEQ ID NO:11.

21. A set of primers according to claim 20, further comprising a first bumper primer comprising SEQ ID NO:7 and a second bumper primer comprising a sequence selected from the group consisting of SEQ ID NO:5 and SEQ ID NO:8.

22. A set of primers according to claim 20, wherein said first and second primers are contained in an aqueous solution.

23. A set of primers for genus-specific amplification of Mycobacterium nucleic acids comprising a first and a second amplification primer, wherein said first amplification primer comprises a nucleotide sequence selected from the group consisting of nucleotides 25 to 40 of SEQ ID NO:3, nucleotides 25 to 39 of SEQ ID NO:4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, and nucleotides 25 to 37 of SEQ ID NO:14 and wherein said second amplification primer comprises a nucleotide sequence selected from the group consisting of nucleotides 25 to 40 of SEQ ID NO:3, nucleotides 25 to 39 of SEQ ID NO:4, nucleotides 25 to 40 of SEQ ID NO:9, nucleotides 25 to 39 of SEQ ID NO:10, nucleotides 25 to 39 of SEQ ID NO:11, nucleotides 25 to 38 of SEQ ID NO:12, nucleotides 25 to 37 of SEQ ID NO:13, and nucleotides 25 to 37 of SEQ ID NO:14.

24. A kit for detecting Mycobacterium nucleic acids comprising:
(a) a set of primers for genus-specific amplification of Mycobacterium nucleic acids according to claim 18 or claim 23;
(b) means for detecting said Mycobacterium nucleic acids using said primer set.

25. A kit according to claim 24 further comprising a detector probe wherein said detector probe comprises a nucleotide sequence selected from the group consisting of SEQ ID NO:6, SEQ ID NO:15 and SEQ ID NO:16.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1464 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:

-continued (A) ORGANISM: Mycobacterium tuberculosis (xi) SEQUENCE DESCRIPTION: SEQ ID NO:1:

GGCGGCGTGC TTAACACATG CAAGTCGAAC GGAAAGGTCT CTTCGGAGAT ACTCGAGTGG 60

CGAACGGGTG AGTAACACGT GGGTGATCTG CCCTGCACTT CGGGATAAGC CTGGGAAACT 120

GGGTCTAATA CCGGATAGGA CCACGGGATG CATGTCTTGT GGTGGAAAGC GCTTTAGCGG 180

TGTGGGATGA GCCCGCGGCC TATCAGCTTG TTGGTGGGGT GACGGCCTAC CAAGGCGACG 240

ACGGGTAGCC GGCCTGAGAG GGTGTCCGGC CACACTGGGA CTGAGATACG GCCCAGACTC 300

CTACGGGAGG CAGCAGTGGG GAATATTGCA CAATGGGCGC AAGCCTGATG CAGCGACGCC 360

GCGTGGGGGA TGACGGCCTT CGGGTTGTAA ACCTCTTTCA CCATCGACGA AGGTCCGGGT 420

TCTCTCGGAT TGACGGTAGG TGGAGAAGAA GCACCGGCCA ACTACGTGCC AGCAGCCGCG 480

GTAATACGTA GGGTGCGAGC GTTGTCCGGA ATTACTGGGC GTAAAGAGCT CGTAGGTGGT 540

TTGTCGCGTT GTTCGTGAAA TCTCACGGCT TAACTGTGAG CGTGCGGGCG ATACGGGCAG 600

ACTAGAGTAC TGCAGGGGAG ACTGGAATTC CTGGTGTAGC GGTGGAATGC GCAGATATCA 660

GGAGGAACAC CGGTGGCGAA GGCGGGTCTC TGGGCAGTAA CTGACGCTGA GGAGCGAAAG 720

CGTGGGGAGC GAACAGGATT AGATACCCTG GTAGTCCACG CCGTAAACGG TGGGTACTAG 780

GTGTGGGTTT CCTTCCTTGG GATCCGTGCC GTAGCTAACG CATTAAGTAC CCCGCCTGGG 840

GAGTACGGCC GCAAGGCTAA AACTCAAAGG AATTGACGGG GGCCCGCACA AGCGGCGGAG 900

CATGTGGATT AATTCGATGC AACGCGAAGA ACCTTACCTG GGTTTGACAT GCACAGGACG 960

CGTCTAGAGA TAGGCGTTCC CTTGTGGCCT GTGTGCAGGT GGTGCATGGC TGTCGTCAGC 1020

TCGTGTCGTG AGATGTTGGG TTAAGTCCCG CAACGAGCGC AACCCTTGTC TCATGTTGCC 1080

AGCACGTAAT GGTGGGGACT CGTGAGAGAC TGCCGGGGTC AACTCGGAGG AAGGTGGGGA 1140

TGACGTCAAG TCATCATGCC CCTTATGTCC AGGGCTTCAC ACATGCTACA ATGGCCGGTA 1200

CAAAGGGCTG CGATGCCGCG AGGTTAAGCG AATCCTTAAA AGCCGGTCTC AGTTCGGATC 1260

GGGGTCTGCA ACTCGACCCC GTGAAGTCGG AGTCGCTAGT AATCGCAGAT CAGCAACGCT 1320

GCGGTGAATA CGTTCCCGGG CCTTGTACAC ACCGCCCGTC ACGTCATGAA AGTCGGTAAC 1380

ACCCGAAGCC AGTGGCCTAA CCCTCGGGAG GGAGCTGTCG AAGGTGGGAT CGGCGATTGG 1440

GACGAAGTCG TAACAAGGTA GCCG 1464

(2) INFORMATION FOR SEQ ID NO:2:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:2:

ACGCGAAGAA CCTT 14

(2) INFORMATION FOR SEQ ID NO:3:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:3:

AACTTAGTAC GGAATCAAGT TGACGTTTGA CATGCACAGG 40

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:4:

TTCATCTTGA GCTTGTATGT TGACGCACCT GCACACAGG        39

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:5:

GCTGACGACA GCCA        14

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:6:

GCGTTCCCTT GTGG        14

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

ACGCGAAGAA CCTTA        15

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:8:

GCTGACGACA GCAA        14

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:9:

CGATTCCGCT CCAGACTTCT CGGGGTTTGA CATGCACAGG        40

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

CGATTCCGCT CCAGACTTCT CGGGTTTGAC ATGCACAGG                                   39

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:11:

CGATTCCGCT CCAGACTTCT CGGGGTTTGA CATGCACAG                                   39

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:12:

ACCGCATCGA ATGCATGTCT CGGGCACCTG CACACAGG                                    38

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

ACCGCATCGA ATGCATGTCT CGGGACCTGC ACACAGG                                     37

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:14:

ACCGCATCGA ATGCATGTCT CGGGCACCTG CACACAG                                     37

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:15:

GGCGTTCCCT TGTGG                                                             15

(2) INFORMATION FOR SEQ ID NO:16:

(i) SEQUENCE CHARACTERISTICS:

-continued

```
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:16:

CCACAAGGGA ACGCC                                                    15
```